(12) United States Patent
Shachaf et al.

(10) Patent No.: US 9,958,327 B2
(45) Date of Patent: May 1, 2018

(54) DECONVOLUTION TO REDUCE THE EFFECTIVE SPOT SIZE OF A SPECTROSCOPIC OPTICAL METROLOGY DEVICE

(71) Applicant: Nanometrics Incorporated, Milpitas, CA (US)

(72) Inventors: Amit Shachaf, Los Gatos, CA (US); Pedro Vagos, Chennevieres (FR); Michael Elad, Kiriat Tivon (IL)

(73) Assignee: Nanometrics Incorporated, Milpitas, CA (US)

( * ) Notice: Subject to any disclaimer, the term of this patent is extended or adjusted under 35 U.S.C. 154(b) by 805 days.

(21) Appl. No.: 14/505,373

(22) Filed: Oct. 2, 2014

(65) Prior Publication Data

US 2016/0097677 A1   Apr. 7, 2016

Related U.S. Application Data

(60) Provisional application No. 62/058,512, filed on Oct. 1, 2014.

(51) Int. Cl.
*G01N 21/00* (2006.01)
*G01J 3/28* (2006.01)
(Continued)

(52) U.S. Cl.
CPC .......... *G01J 3/28* (2013.01); *G01N 21/8851* (2013.01); *G01N 21/956* (2013.01); *G03F 7/70625* (2013.01)

(58) Field of Classification Search
CPC .... G01J 3/28; G03F 7/70625; G01N 21/8851; G01N 21/956
See application file for complete search history.

(56) References Cited

U.S. PATENT DOCUMENTS 4,656,358 A   4/1987  Divens et al.
5,455,673 A   10/1995 Alsmeyer et al.
(Continued)

FOREIGN PATENT DOCUMENTS

EP   1 947 604 A1   7/2008

OTHER PUBLICATIONS

International Search Report and Written Opinion dated Dec. 7, 2015 for International Application No. PCT/US2015/051774 filed on Sep. 23, 2015, 11 pages.
(Continued)

*Primary Examiner* — Elias Desta
(74) *Attorney, Agent, or Firm* — Silicon Valley Patent Group LLP

(57) ABSTRACT

The effective spot size of a spectroscopic metrology device is reduced through deconvolution of a measurement spectra set acquired from a measurement target combined with a training spectra set obtained from a training target. The measurement spectra set may be obtained using sparse sampling of a grid scan of a measurement target. The training spectra set is obtained from a grid scan of a training target that is similar to the measurement target. The training spectra set and the measurement spectra set include spectra from different grid nodes. Deconvolution of the measurement spectra and the training spectra sets produces an estimated spectrum for the measurement target that is an estimate of a spectrum from the measurement target produced with incident light having an effective spot size that is smaller than the actual spot size. One or more characteristics of the measurement target may then be determined using the estimated spectrum.

42 Claims, 11 Drawing Sheets

(51) Int. Cl.
　　　*G01N 21/88*　　(2006.01)
　　　*G01N 21/956*　(2006.01)
　　　*G03F 7/20*　　 (2006.01)

(56)　　　　　References Cited

U.S. PATENT DOCUMENTS

| | | |
|---|---|---|
| 5,760,901 A | 6/1998 | Hill |
| 6,489,611 B1 | 12/2002 | Aumond et al. |
| 6,661,004 B2 | 12/2003 | Aumond et al. |
| 7,145,654 B2 | 12/2006 | Norton |
| 7,522,272 B2 * | 4/2009 | Wolf ............... G01B 11/0666 356/73 |
| 8,259,297 B1 | 9/2012 | Yarussi |
| 8,614,790 B2 | 12/2013 | Berlatzsky et al. |
| 2004/0090874 A1 | 5/2004 | Balasubramian et al. |
| 2006/0043291 A1 * | 3/2006 | Peng ..................... H01J 37/28 250/310 |
| 2008/0024781 A1 | 1/2008 | Zangooie et al. |
| 2010/0153323 A1 | 6/2010 | Hennessy et al. |
| 2013/0321908 A1 | 12/2013 | Babacan et al. |

OTHER PUBLICATIONS

Jiang, W-L et al. (Nov. 1993). "A Novel Technique for Deconvoluting Spectra," *Science in China (Series A)* 36(11):1329-1339.

* cited by examiner

DECONVOLUTION TO REDUCE THE EFFECTIVE SPOT SIZE OF A SPECTROSCOPIC OPTICAL METROLOGY DEVICE

CROSS-REFERENCE TO RELATED APPLICATION(S)

This application claims priority under 35 USC 119 to U.S. Provisional Application No. 62/058,512, filed Oct. 1, 2014, and entitled "Deconvolution to Reduce the Effective Spot Size of a Spectroscopic Optical Metrology Device," which is incorporated herein by reference in its entirety.

BACKGROUND

Background Field

Embodiments of the subject matter described herein are related generally to optical metrology, and more particularly, to the reduction of spot size of an optical metrology device.

Relevant Background

Semiconductor and other similar industries, often use optical metrology equipment to provide non-contact evaluation of substrates during processing. Optical metrology techniques, such as ellipsometry and reflectometry, typically operate by illuminating a sample with a probe beam of electromagnetic radiation and then detecting and analyzing the reflected and/or transmitted energy. The probe beam may be polarized or unpolarized radiation, and may include one or more wavelengths of radiation. Ellipsometry typically measures changes in the polarization state of the reflected beam after interacting with the sample, while reflectometry measures changes in the magnitude of the reflected beam.

It is desirable with optical metrology for the measurement spot produced by an optical metrology device to fall completely within a target area on the sample under test. The measurement spot is the area on the surface of the sample from which light is reflected (or transmitted through) and subsequently received by the detector of the optical metrology device. The probe beam does not produce a measurement spot with sharp edges or boundaries; instead, the probe beam has an intensity distribution such that the total beam power is confined in a small area, i.e., the measurement spot. The size of the measurement spot is conventionally determined by the optical system of the optical metrology device.

The target area that is measured by the optical metrology device may be a specifically designed target, e.g., placed within scribe lines between the processed dies on the substrate or may be a specific region that is within the chips. The target area may be determined by structures or features of the sample produced during processing. The target area may be defined by a physical box or area that is present on the sample, e.g., as a square or box that is manufactured on the surface of a sample, or may be merely an undefined region on the sample that is to be measured. It is generally desirable for accuracy of the measurement to have the measurement spot fully confined to the target area. However, as geometries of devices in semiconductor and similar industries continues to shrink, the size of the target areas likewise shrinks making it more difficult to produce measurement spots that are spatially confined to the target area. Moreover, redesigning the optical system to reduce the spot size produced by the optical metrology device is an expensive and time consuming task.

SUMMARY

The effective spot size of a spectroscopic metrology device is reduced through deconvolution of a measurement spectra set acquired from a measurement target combined with a training spectra set obtained from a training target. The measurement spectra set may be obtained using sparse sampling of a grid scan of a measurement target. The training spectra set is obtained from a grid scan of a training target that is similar to the measurement target. The training spectra set and the measurement spectra set include spectra from different grid nodes. Deconvolution of the measurement spectra and the training spectra sets produces an estimated spectrum for the measurement target that is an estimate of a spectrum from the measurement target produced with incident light having an effective spot size that is smaller than the actual spot size. One or more characteristics of the measurement target may then be determined using the estimated spectrum.

In one implementation, a method of spectroscopic metrology includes obtaining a training spectra set from a grid scan of a training target, wherein the grid scan of the training target is performed using a spectroscopic metrology device with incident light having a measurement spot size, wherein the training spectra set comprises spectra from a first set of grid nodes in the grid scan; performing a sparse sampling of the grid scan of a measurement target using the spectroscopic metrology device with the incident light having the measurement spot size to acquire a measurement spectra set, wherein the measurement spectra set comprises spectra from a second set of grid nodes in the grid scan, wherein the first set of grid nodes and the second set of grid nodes are different; performing a deconvolution of a combination of the measurement spectra set and the training spectra set to produce an estimated spectrum of the measurement target that is an estimate of a spectrum from the measurement target produced with the incident light having an effective measurement spot size that is smaller than the measurement spot size; and determining one or more characteristics of the measurement target using the estimated spectrum.

In one implementation, a spectroscopic metrology device includes a broadband illumination source to produce broadband illumination; an optical system that focuses the broadband illumination into incident light with a measurement spot size; a spectrometer that detects a spectrum of the broadband illumination after being incident on a sample; and a processor coupled to receive the spectrum from the spectrometer, the processor configured to cause the optical system and spectrometer to perform a grid scan of a training target to obtain a training spectra set, wherein the training spectra set comprises spectra from a first set of grid nodes in the grid scan; the processor further configured to cause the optical system and spectrometer to perform a sparse sampling of the grid scan of a measurement target to acquire a measurement spectra set, wherein the measurement spectra set comprises spectra from a second set of grid nodes in the grid scan, wherein the first set of grid nodes and the second set of grid nodes are different; to perform a deconvolution of a combination of the measurement spectra set and the training spectra set to produce an estimated spectrum of the measurement target that is an estimate of a spectrum from the measurement target produced with the incident light having an effective measurement spot size that is smaller than the measurement spot size; and to determine one or more characteristics of the measurement target using the estimated spectrum.

In one implementation, a method of producing deconvolution kernel weights for deconvolution of spectral signals from a spectroscopic metrology device includes performing a grid scan of one or more calibration targets using the spectroscopic metrology device to acquire a calibration spectra set, wherein the calibration spectra set comprises spectra from each grid node in the grid scan; and using the calibration spectra set to determine the deconvolution kernel weight for each grid node in the grid scan.

DETAILED DESCRIPTION

Figure 1:
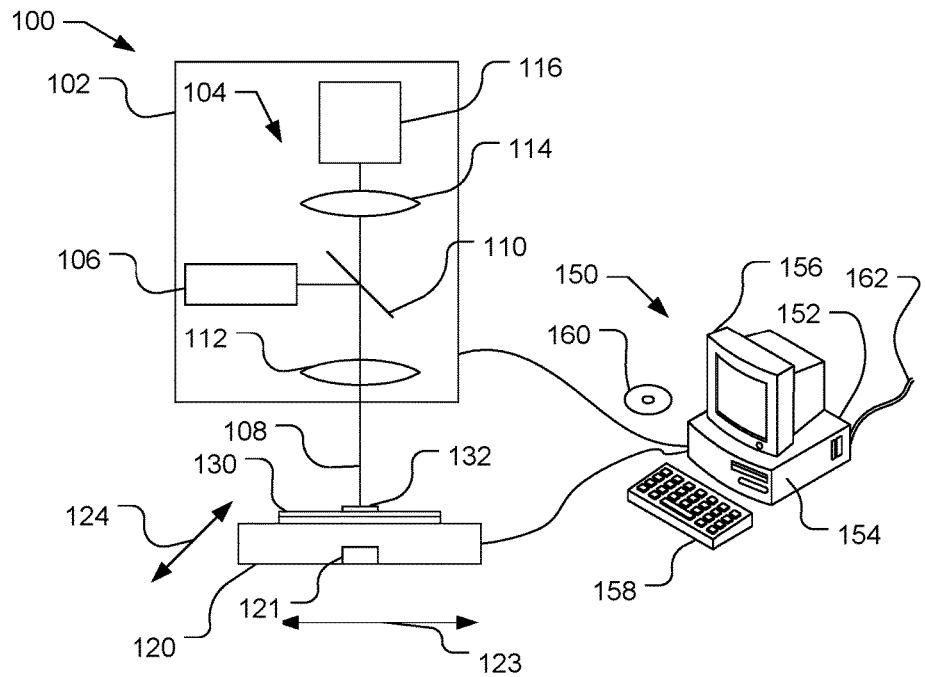
FIG. 1 shows a schematic view of a spectroscopic metrology device that may reduce the effective spot size of a measurement spot through a small spot by deconvolution process.

FIG. 1 shows a schematic view of an optical metrology device 100, including an optical head 102 coupled to a computer 150, such as a workstation, a personal computer, central processing unit or other adequate computer system, or multiple systems, and that reduces the effective spot size of a measurement spot through deconvolution of the spectra detected from the measurement target and a training spectra set obtained from one or more training targets. The optical metrology device 100 illustrated in FIG. 1 is, e.g., a spectroscopic reflectometer. If desired, multiple optical heads, i.e., different metrology devices, may be combined in the same metrology device 100. The computer 150 may also control the movement of a stage 120 that holds the sample 130 via actuators 121 and/or the optical head 102. The stage 120 may be capable of horizontal motion in either Cartesian (i.e., X and Y) coordinates, as indicated by arrows 123 and 124, or Polar (i.e., R and θ) coordinates or some combination of the two. The stage 120 and/or optical head 102 may also be capable of vertical motion, e.g., for focusing.

The optical head 102 may include an optical system 104 including a broadband light source 106, such as a Xenon Arc lamp and/or a Deuterium lamp, and a detector 116, such as a spectrometer. In operation, light produced by the light source 106 may be directed along an optical axis 108, e.g., via beam splitter 110, toward the sample 130 which includes a target 132. An objective 112 focuses the light onto the target 132 and receives light that is reflected from the target 132. The reflective light may pass through the beam splitter 110 and is focused with lens 114 onto the detector 116. The detector 116 provides a spectroscopic signal to the computer 150. The objective 112, beam splitter 110, lens 114, and detector 116 are merely illustrative of typical optical elements that may be used. Additional optical elements, such as a polarizer and/or analyzer, may be used if desired. Moreover, generally, additional optical elements such as field stops, lenses, etc. may be present in the optical system 104.

The optical system 104 produces a measurement spot on the surface of the sample 130. The measurement spot has a spot size that is physically limited by the components of the optical system 104. In general, it is desirable for the measurement spot size to be smaller than the size of the target 132 so that the reflected light received by the optical system is only from the target 132 and does not include light reflected from the target neighborhood, i.e., areas on the sample 130 outside and around the target 132. As the geometries of devices in semiconductor and similar industries continues to shrink, the size of targets similarly decreases making it more difficult to produce a measurement spot size that is smaller than the target. Using deconvolution of specta detected from the measurement target and a training spectra set obtained from one or more training targets measured at multiple locations on and near the target, the effective size of the measurement spot may be reduced, e.g., to be smaller than the target. The spectral signal from the measurement target 132 may be provided to a computer 150, along with a training spectra set from a measured training target. The computer 150 may then reduce the effective spot size of the measurement spot through deconvolution of the combined spectrum or spectra from the measurement target and the training spectra set. After reducing the effective spot size, the computer 150 (or a different computer) may then conventionally determine the desired characteristic of the sample.

The computer 150 includes a processor 152 with memory 154, as well as a user interface including e.g., a display 156 and input devices 158. The training spectra set measured from a training target and the measurement spectra set, as well as the resulting estimated spectrum and one or more characteristics of the measurement target may be stored at least temporarily in memory 154 or in non-transitory computer-usable storage medium 160. Additionally, non-transitory computer-usable storage medium 160 may have computer-readable program code embodied thereon and may be used by the computer 150 for causing the processor to control the metrology device and to perform the functions described herein. The data structures and software code for automatically implementing one or more acts described in this detailed description can be implemented by one of ordinary skill in the art in light of the present disclosure and stored, e.g., on a computer readable storage medium 160, which may be any non-transitory device or medium that can store code and/or data for use by a computer system such as processor 152. The computer-usable storage medium 160 may be, but is not limited to, magnetic and optical storage devices such as disk drives, magnetic tape, compact discs, and DVDs (digital versatile discs or digital video discs). A communication port 162 may also be used to receive instructions that are stored in memory 154 or other storage in computer 150 and used to program the computer 150 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Figure 2:
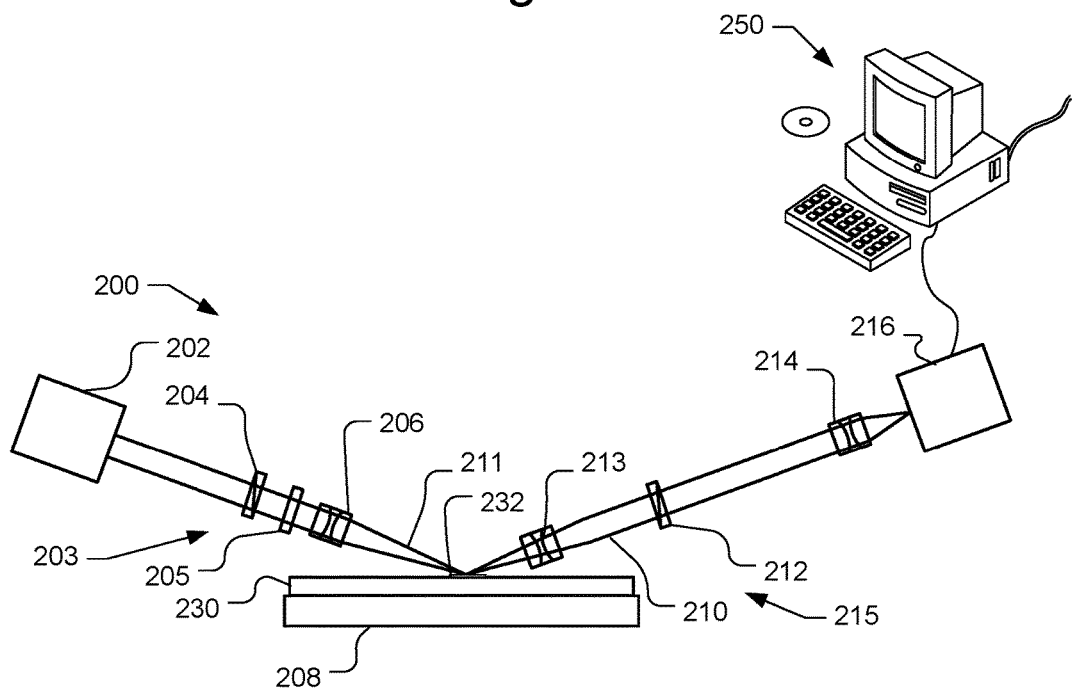
FIG. 2 shows a schematic view of another spectroscopic metrology device that may reduce the effective spot size of a measurement spot through small spot by deconvolution process.

FIG. 2 shows a schematic view of another optical metrology device 200, illustrated as a spectroscopic ellipsometer, that may have the effective spot size of its measurement spot reduced through deconvolution by computer 250, which may be substantially similar to computer 150 discussed above, but configured to operate a spectroscopic ellipsometer as opposed to a spectroscopic reflectometer.

Ellipsometer 200 is illustrated as including a broadband light source 202 and a polarization state generator 203 with a polarizer 204 and a rotating compensator 205, as well as a lens system 206 that focuses the illuminating light 211 into a measurement spot on the surface of a sample 230 that is positioned on a stage 208. The incident illuminating light 211 has a known polarization state due to the polarizer 204 and rotating compensator 205. The polarization state of the light reflected by the sample 201 is analyzed by a polarization state analyzer 215, e.g., by passing the reflected light 213 through another polarizer 212, commonly referred to as analyzer 212, after passing through another lens system 210. After passing through the analyzer 212, the reflected light 213 is focused by a lens system 214 on a detector 216, which is coupled to the computer 250. In use, a sample under test will change the polarization state of the incident light, which will change the intensity and phase of the resulting signal from the detector 216. Using the change in intensity and phase, the material properties of the sample 230 may be determined, which is the essence of ellipsometry and is well known in the art.

The optical system of the spectroscopic ellipsometer 200 produces a measurement spot on the surface of the sample 230, which includes a measurement target 232. Again, while the spot size of the measurement spot is physically limited by the optical system of the spectroscopic ellipsometer 200, the effective spot size of the measurement, however, may be reduced by the computer 250 through deconvolution of the specta detected from the measurement target 232 and a training spectra set obtained from one or more training targets It should be understood that while a spectroscopic reflectometer and spectroscopic ellipsometer are specifically discussed herein, the small spot by deconvolution process used to reduce the effective spot size of a spectroscopic metrology device is not limited thereto. The reduction of the effective spot size disclosed herein may be applicable to any desired spectroscopic metrology device.

Figures 3A, 3B:
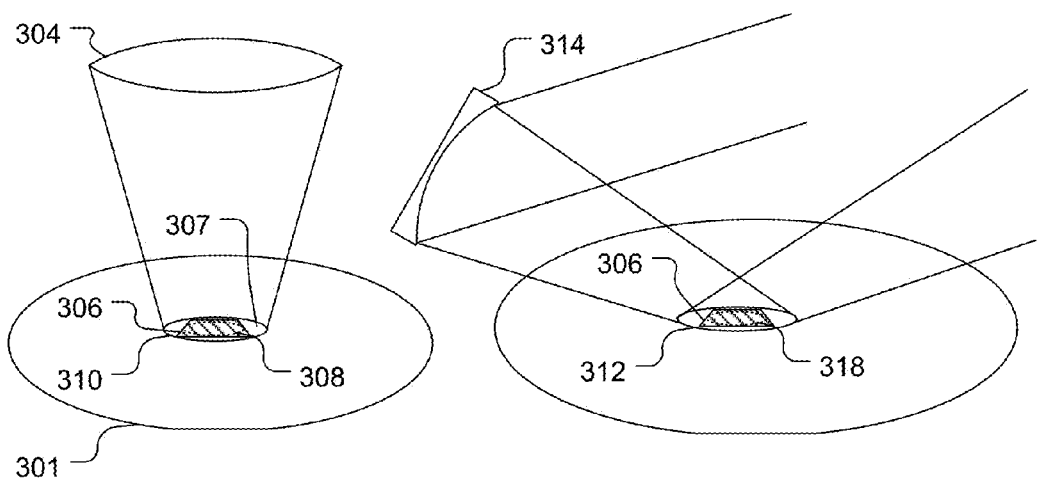
FIGS. 3A and 3B illustrates a measurement spots on the surface of a sample produced by normal incidence and oblique incidence illumination, respectively, along with a reduction in the spot size.

FIG. 3A illustrates a measurement spot 310 on the surface of a sample 301 produced by normal incidence illumination, such as that produced by metrology device 100 in FIG. 1. The measurement spot 310 is illustrated as being produced with a refractive lens 304, but a reflective lens may be used. As illustrated, the measurement spot 310 is incident on a measurement target 306, which is shown with cross-hatching and with a greatly exaggerated size relative to the sample 301 for clarity. The measurement target 306 may be determined by structures or features of the sample 301 and may be a physically designated area on the sample, e.g., as a square or box that is manufactured on the surface of a sample, or it may be merely an undefined region on the sample that is to be measured. The spot size of the measurement spot 310 is determined the optical system of the metrology device, e.g., represented by lens 304. As can be seen in FIG. 3A, the spot size of the measurement spot 310 is illustrated as being larger than the measurement target 306. Thus, the signal received by the metrology device will include light reflected from the measurement target 306 as well as neighborhood locations 307, i.e., areas outside and around the measurement target 306. However, through a deconvolution of a training spectra set combined with the spectroscopic measurement from the measurement spot 310, the effective spot size of the measurement spot 310 may be reduced, e.g., illustrated as spot 308 with dashed lines that is smaller than the measurement target 306.

FIG. 3B is similar to FIG. 3A, showing a measurement spot 312 that may be produced by oblique illumination, such as that produced by metrology device 200 in FIG. 2. The measurement spot 312 is illustrated as being produced with a reflective lens 314, but a refractive lens may be used if desired. The spot size of the measurement spot 312 is determined, e.g., by lens 314, and is illustrated as being greater than the measurement target 306. Through a deconvolution of the combined spectroscopic measurement of the measurement target 306 and a training spectra set, however, the effective spot size of the measurement spot 312 may be reduced to a spot size 318, which is illustrated as being smaller than the measurement target 306.

Figure 4:
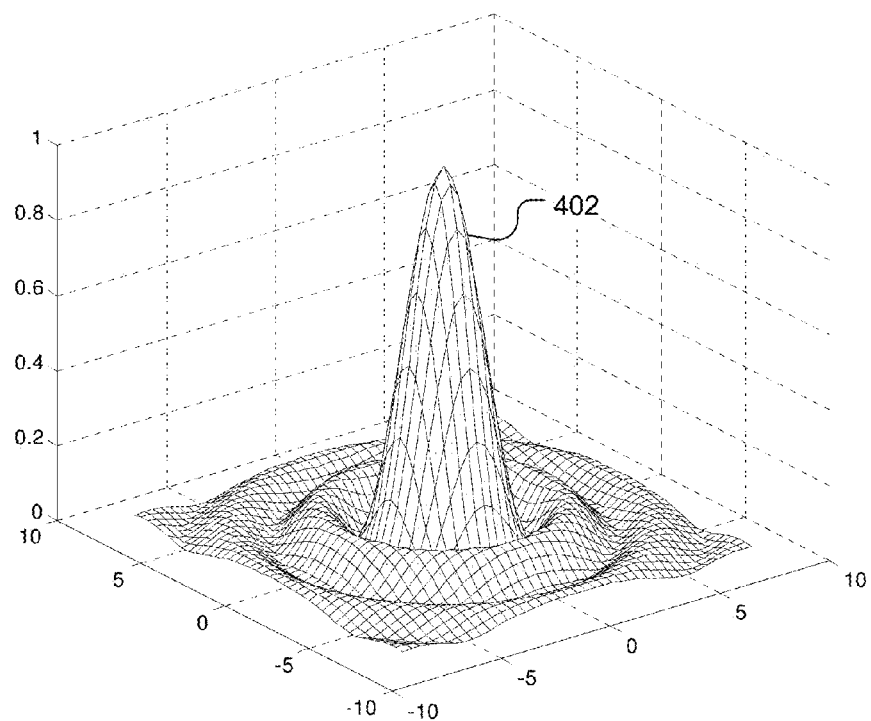
FIG. 4 illustrates a normalized illumination intensity 2-dimensional profile of a measurement spot with respect to position for a single wavelength.

It should be understood that a typical measurement spot, such as that illustrated in FIGS. 3A and 3B, does not have sharp edges or boundaries. The probe beam produced by the optical system of an optical metrology device has an intensity distribution with the total beam power confined in a small area, i.e., the measurement spot. FIG. 4, by way of example, illustrates a normalized illumination intensity 2-dimensional profile of a measurement spot 402 with respect to position for a single wavelength. As can be seen, the illumination intensity profile includes a main lobe that may be surrounded by secondary maxima, which are the result of the diffraction limits of the illumination and/or detector optics. The measurement spot size may be determined as the full width half maximum (FWHM) of the central portion of the intensity profile.

Figure 5A:
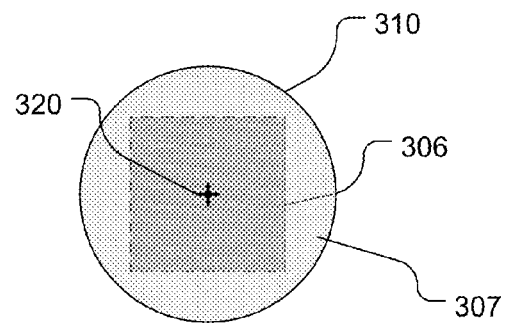
FIG. 5A illustrates a top view of a measurement spot that is larger than a measurement target.
Figure 5B:
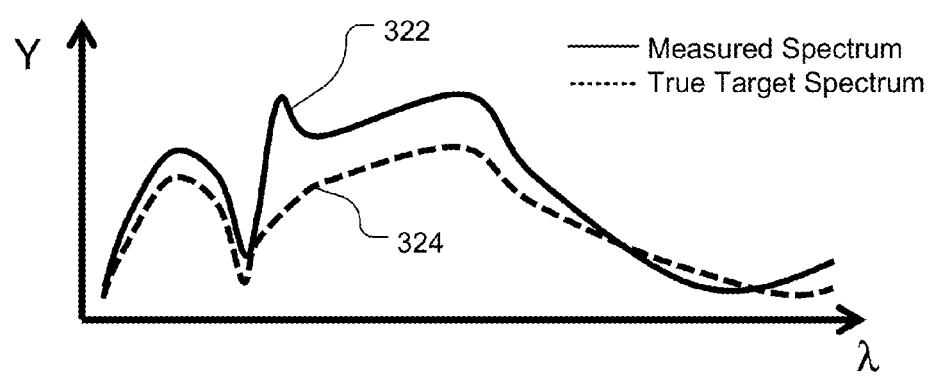
FIG. 5B is a graph illustrating the measured spectrum from the measurement target using the measurement spot from FIG. 5A.

FIG. 5A illustrates a top view of a measurement spot 310 produced by an optical metrology device. The measurement spot 310 is illustrated as centered on a location (illustrated with cross pattern 320) that is in the center of the measurement target 306. FIG. 5B is a graph illustrating the measured spectrum 322 Y(λ) from the measurement target 306 using the measurement spot 310. The measured spectrum 322 may be, e.g., an OCD (optical critical dimension) spectrum, spectral reflectivity, spectral ellipsometer, Mueller matrix element, etc. By way of comparison, the "true" target spectrum 324 is also illustrated in FIG. 5B, where the true target spectrum 324 is the spectrum that would be produced if the measurement spot 310 illuminated only the measurement target 306. The measurement spot 310, however, is incident on both the measurement target 306 and target neighborhood locations 307, i.e., areas outside the measurement target 306, and consequently, the measured spectrum 322 is a mixture of the true target spectrum 324 and the target neighborhood spectrum.

Figure 6:
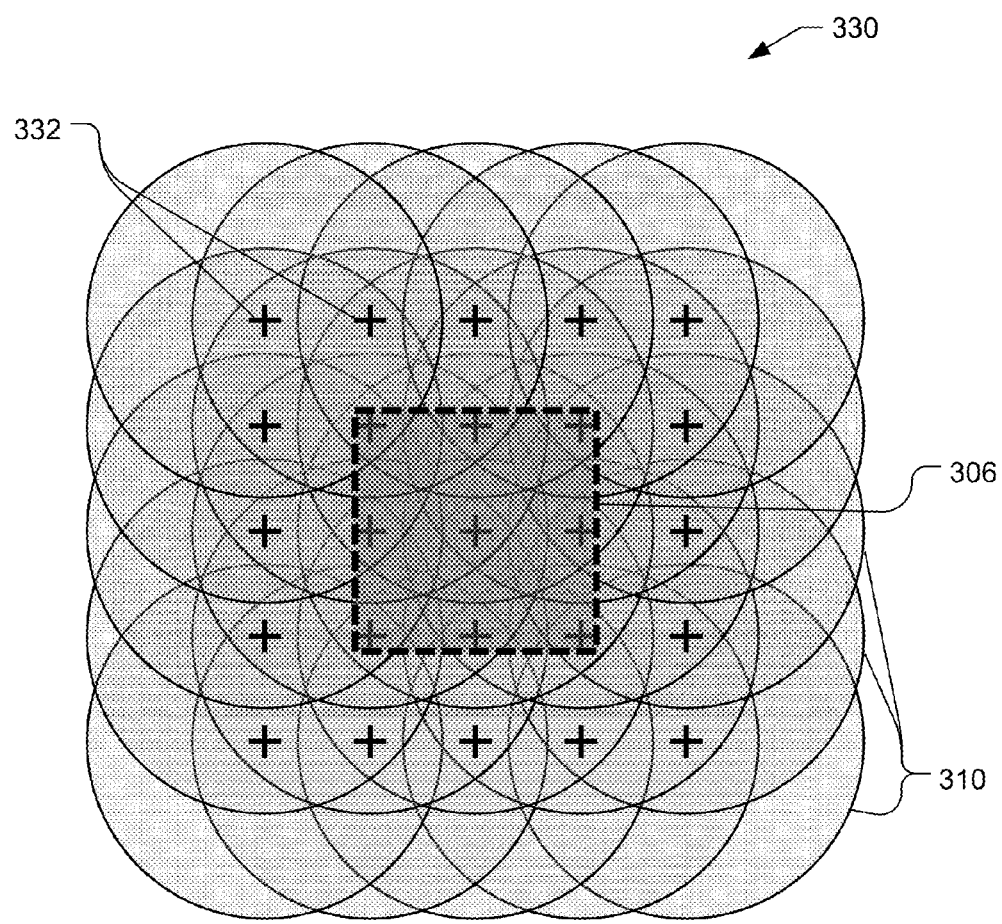
FIG. 6 illustrates a grid scan with an N×N array of grid nodes of a measurement target by which N×N specta is acquired.

To reduce the effective spot size of the measurement spot, a deconvolution process is used. Deconvolution of the measurement spot may use specta detected at multiple locations on and near the measurement target 306. By way of example, N×N spectra may be acquired by measuring the spectral signal at grid nodes of an N×N grid over the measurement target 306. FIG. 6, by way of example, illustrates a grid scan 330 of the measurement target 306, in which spectra may be separately measured (as illustrated by the measurement spots 310) from each grid node 332 (illustrated with cross patterns) of the 5×5 grid array (i.e., N=5). During measurement, the center of the measurement spot 310 is aligned with a grid node 332 and the spectrum measured before the measurement spot 310 is scanned to the next grid node 332, e.g., by moving the sample, the optical system of the measurement device or both. FIG. 6 illustrates a symmetrical 5×5 array of grid nodes 332 centered on the measurement target 306, but other sizes of the array may be used, e.g., 7×7, 9×9, . . . 21×21, etc. Moreover, the grid scan may have other shapes (e.g., N×M or other shapes), positions, and orientations than that illustrated in FIG. 6. The grid nodes 332 in the array should be close enough that the measurement spots 310 when produced at horizontally, vertically, and diagonally adjacent grid nodes 332, should overlap, i.e., the distance between horizontally or vertically adjacent grid nodes 332 should be less than or equal to $$\frac{\sqrt{2}}{2} R$$

where R is the diameter of the measurement spot 310. For the sake of simplicity, the grid scan will be generally referred to as an N×N grid scan. Thus, N×N spectra $Y_{n,m}(\lambda)$ may be acquired, where $Y_{n,m}(\lambda)$, where "n,m" are the grid node coordinates.

The "true" spectrum from the measurement target 306 may be estimated with deconvolution of the N×N spectra $Y_{n,m}(\lambda)$, which eliminates, or at least reduces, the influence of spectra from the target neighborhood locations, i.e., areas outside the measurement target 306. The spectrum produced through a deconvolution of the N×N spectra $Y_{n,m}(\lambda)$ is equivalent to a spectrum at the center of the measurement target 306 produced using a measurement spot having a smaller spot size, and is therefore sometimes referred to as small spot by deconvolution. In other words, the effective spot size of the measurement spot 310 is reduced. The effective spot size of the measurement spot 310 is approximately the size of the distance between grid nodes, at best.

For example, a space of 5 μm between grid nodes 332 will produce an effective spot size of approximately 5 μm. Accordingly, by decreasing the distance between nodes, e.g., by increasing N without increasing the area of the grid scan, the effective spot size of the measurement spot 310 may be reduced.

A linear or non-linear deconvolution may be used. In either case, the deconvolution uses a "deconvolution kernel", i.e. a collection of constants that need to be found before applying the deconvolution algorithm. The deconvolution kernel does not depend on the target being measured, but depends only on the illumination intensity profile (i.e., intensity as a function of position as illustrated in FIG. 4) produced by the optical system of the optical metrology device and the tool response, i.e., the detector signal as a function of illumination intensity profile. The constants of the deconvolution kernel are sometimes referred to as "weights." An example of linear deconvolution is given by the formula:

$$Y_o(\lambda) = \sum_{n,m} w_{n,m} \cdot Y_{n,m}(\lambda) \qquad \text{eq. 1}$$

where $w_{n,m}$ is the weight associated with the grid node (n,m), $Y_{n,m}(\lambda)$ is the spectrum measured at the grid node (n,m) and $Y_o(\lambda)$ is the estimated spectrum of the measurement target. An example of non-linear deconvolution is given by the formula:

$$Y_o(\lambda) = \sum_{k=0} \sum_{n,m} w_{n,m}^{(k)} \cdot [Y_{n,m}(\lambda)]^k \qquad \text{eq. 2}$$

where $w^{(k)}_{n,m}$ are the weights of order "k" for the node grid node (n,m). Other deconvolution formulas may be applied as well.

Deconvolution, whether linear or non-linear, requires a prior knowledge of the set of weights "$w_{n,m}$" for the optical metrology device. If the illumination intensity profile of the optical metrology device is a function of wavelength, or if the response of the tool is wavelength dependent, then to achieve a proper deconvolution it is necessary to have a set of weights for each wavelength $w_{n,m}(\lambda)$. The weights may be found either experimentally or theoretically or a combination of experimental and theoretical.

Figure 7:
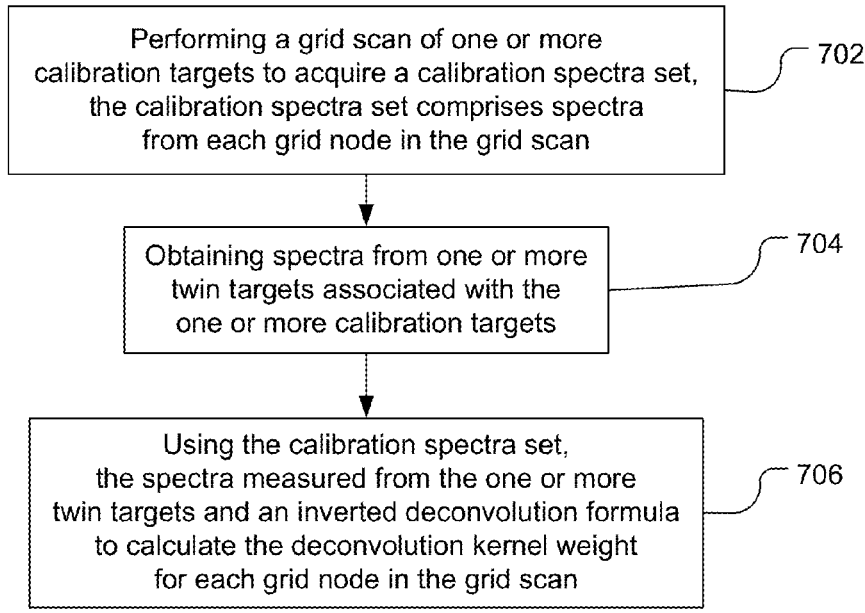
FIG. 7 is a flow chart illustrating a process of determining the deconvolution kernel weights experimentally using a calibration procedure.

FIG. 7 is a flow chart illustrating a process of determining the deconvolution kernel weights experimentally using a calibration procedure. A grid scan of one or more calibration targets is performed using a spectroscopic metrology device to acquire a calibration spectra set (702). The calibration spectra set includes spectra from each grid node in the grid scan, e.g., N×N spectra. The spectroscopic metrology device produces incident light having a measurement spot size that may be larger than desired, e.g., larger than a measurement target. Because the calibration procedure is being used to determine the deconvolution kernel weights for the optical metrology device, the calibration target need not be the same as, or even similar to, the measurement target, although it may be advantageous if the calibration target is the same size as the measurement target. The "true" spectrum from each calibration target is known, i.e., the spectrum of the calibration target is known without being perturbed by spectra from the neighborhood locations. One way to determine the "true" spectrum from a calibration target is to measure a "twin" target, i.e., a target that is the same as the calibration target, e.g., made with the same fabrication process, but is larger than the measurement spot size. It may be advantageous for the twin target to be on the same wafer as the calibration target. Moreover, it may be advantageous for each calibration target to have an associated twin target that is located nearby, e.g., to minimize or avoid process variation across the wafer. Thus, spectra from one or more twin targets associated with the one or more calibration targets is obtained (704), where each twin target has a same material and geometry configuration as a calibration target with which the twin target is associated and each twin target is larger than the measurement spot size. As the twin target is larger than the measurement spot size and is made from the same fabrication process as the calibration target, the measured spectra from the twin targets may be presumed to be the true target spectrum for the calibration target. If more than one calibration target is used in the calibration process, spectra are obtained from a twin target associated with each calibration target. The deconvolution kernel weight for each grid node in the grid scan is calculated using the calibration spectra set, the spectra measured from the one or more twin targets and an inverted deconvolution formula (706).

Figure 8:
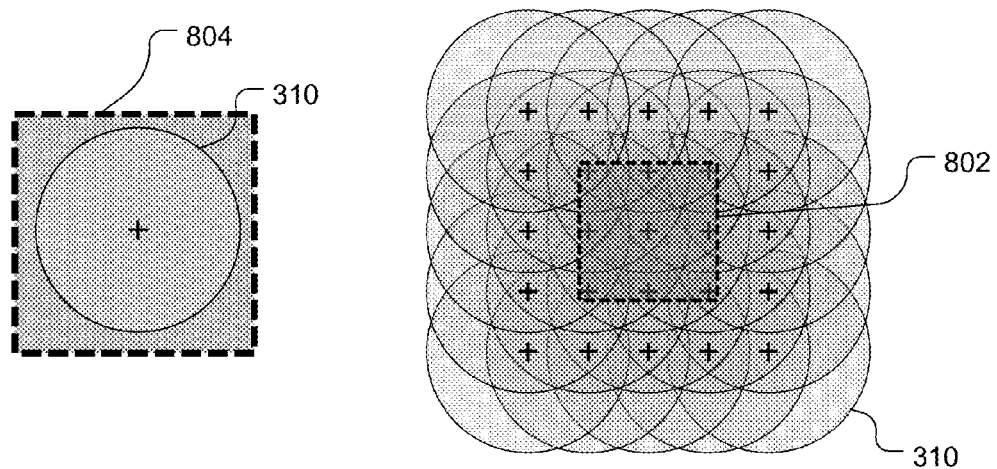
FIG. 8 graphically illustrates an example of the calibration process of FIG. 7.

FIG. 8 illustrates an example of a calibration process of finding the deconvolution kernel weights experimentally for a small spot by deconvolution process using a 5×5 grid scan of a calibration target 802. With a linear deconvolution formula, as shown in equation 1, and a 5×5 grid scan, 25 weights will be determined for the deconvolution kernel for each wavelength, assuming wavelength dependency of the optical system or the response function of the optical metrology device. FIG. 8 illustrates a grid scan of one calibration target 802 with the measurement spot 310 to acquire the calibration spectra set for the calibration target 802, as per step 702 in FIG. 7. Additionally, FIG. 8 illustrates obtaining a spectrum from a twin target 804 with measurement spot 310 as per step 704 in FIG. 7. The twin target 804 is associated with the calibration target 802, e.g., the twin target 804 is near to and produced by the same fabrication process as the calibration target 802, and is larger than the measurement spot 310. Accordingly, the measured spectrum from the twin target 804 may be presumed to be the "true" spectra $Y_o$ for the calibration target 802. In the present example, a number of different calibration targets, e.g., 30, is used, where the true spectrum for each calibration target is known due to obtaining spectra from associated twin targets. Thus, the calibration spectra set is acquired for each of the 30 calibration targets for which the "true" spectra $Y_o^{(t)}$ is known, where "t" is the target number; t=1, 2, . . . 30. Accordingly, equation 1 becomes a system of 30 linear equations, where there is system of equations per wavelength. By replacing the indices "n,m" by a single index "d", e.g., d=1, 2, . . . 25, the system of equations for each wavelength may be written as:

$$Y_o^{(t)} = \sum_{d=1}^{25} w_d \cdot Y_d^{(t)}. \qquad \text{eq. 3}$$

Using matrix notation equation 3 (for a given wavelength) may be written as:

$$Y_o = Y^T \cdot W \qquad \text{eq. 4}$$

where $Y_o$ is the column vector of the 30 values $Y_o^{(t)}$, W is the column vector of the 25 weights $w_d$, Y is a 25×30 matrix of the calibration spectra set acquired for each target, i.e., each column represents a different calibration target t and each row represents a grid node d, and T is the transpose operator. Equation 4 may be inverted to give the weights as:

$$W = (Y \cdot Y^T)^{-1} \cdot Y \cdot Y_o. \qquad \text{eq. 5}$$

Thus, as per step 706 in FIG. 7, the deconvolution kernel weight for each grid node in the grid scan may be calculated using the calibration spectra set, the spectra measured from the one or more twin targets and an inverted deconvolution formula given by equation 5.

Figure 9:
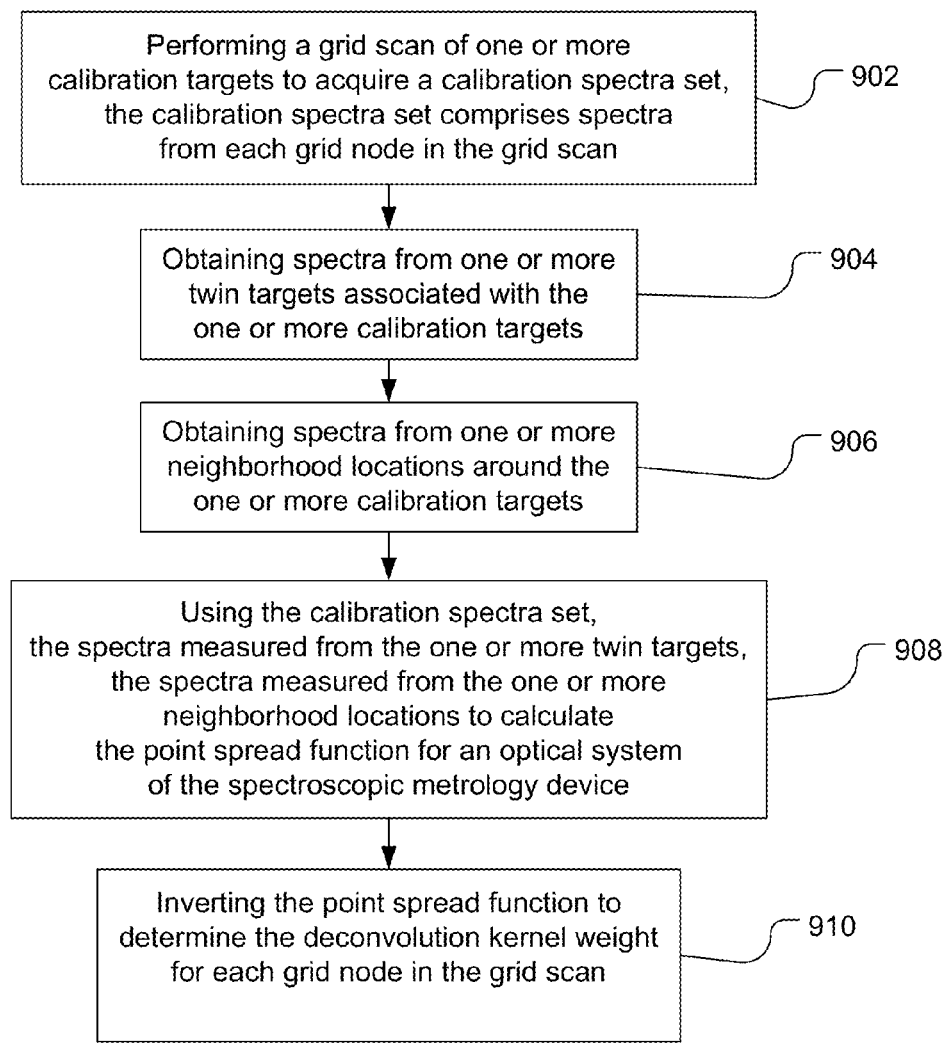
FIG. 9 is a flow chart illustrating another processes of determining the deconvolution kernel weights experimentally using a calibration procedure.
Figure 10:
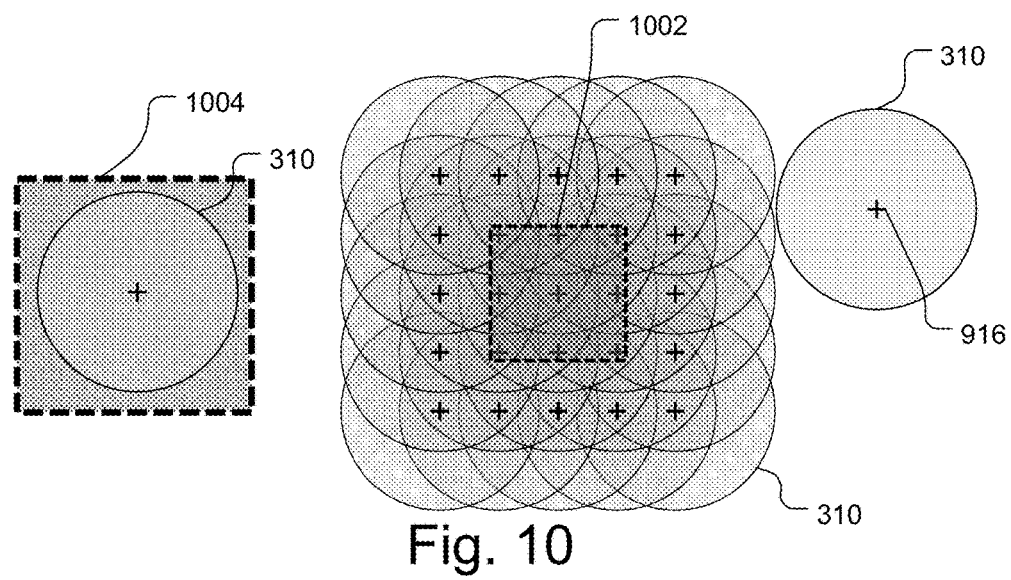
FIG. 10 graphically illustrates an example of the calibration process of FIG. 9.

FIG. 9 illustrates another processes of determining the weights of the deconvolution kernel experimentally using a calibration procedure in which an optical point spread function (PSF) of the optical metrology device is determined and inverted to obtain the weights. FIG. 10 illustrates an example of the calibration process of FIG. 9 using a 5×5 grid scan. As illustrated in FIG. 9, a grid scan of one or more calibration targets is performed using a spectroscopic metrology device to acquire a calibration spectra set (902), as discussed above in FIG. 7. FIG. 10 illustrates a grid scan of a calibration target 1002 with the measurement spot 310 to acquire a calibration spectra set, as per step 902 in FIG. 9. As discussed above in FIG. 7, the "true" spectrum from each calibration target is determined, e.g., by the spectra from one or more twin targets associated with the one or more calibration targets is obtained (904), where each twin target has a same material and geometry configuration as a calibration target with which the twin target is associated and each twin target is larger than the measurement spot size. FIG. 10 illustrates a spectroscopic measurement of a twin target 1004 associated with the calibration target 1002 with measurement spot 310. Additionally, as illustrated in FIG. 9, spectra are obtained from one or more neighborhood locations around the one or more calibration targets (906). As illustrated in FIG. 10, spectra are obtained from a neighborhood location illustrated by position 1006. The neighborhood location 916 is an area outside of the calibration target 1002 (and outside the twin target 1004), where the areas around the calibration target 1002 are uniform and sufficiently separated from other structures that the spectra from the neighborhood location may be measured accurately (without being corrupted by other structures on the wafer). The point spread function for the optical system of the metrology device is calculated using the calibration spectra set, the spectra measured from the one or more twin targets, the spectra measured from the one or more one or more neighborhood locations (908). The point spread function is inverted to determine the deconvolution kernel weight for each grid node in the grid scan (910).

Figure 11:
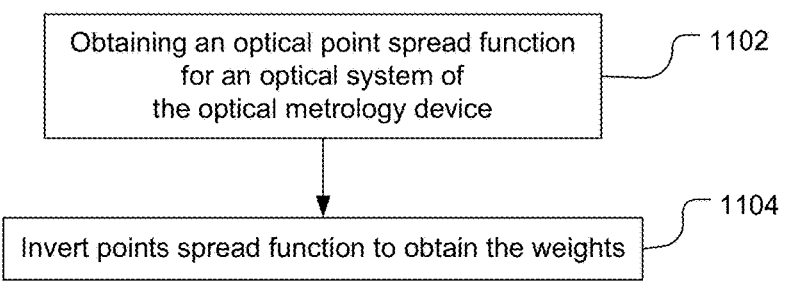
FIG. 11 is a flow chart illustrating a process of theoretically determining the deconvolution kernel weights.

FIG. 11 is a flow chart illustrating a process of theoretically determining the weights of the deconvolution kernel. As illustrated, a point spread function is obtained for an optical system of the spectroscopic metrology device (1102). For example, the optical point spread function may be obtained, e.g., by performing an optical simulation for the optical system of the optical metrology device. Alternatively, the optical point spread function may be obtained, e.g., from a third party, such as the manufacturer of the optical system of the optical metrology device. The point spread function is mathematically inverted to determine the deconvolution kernel weight for each grid node in the grid scan (1104).

Figure 12:
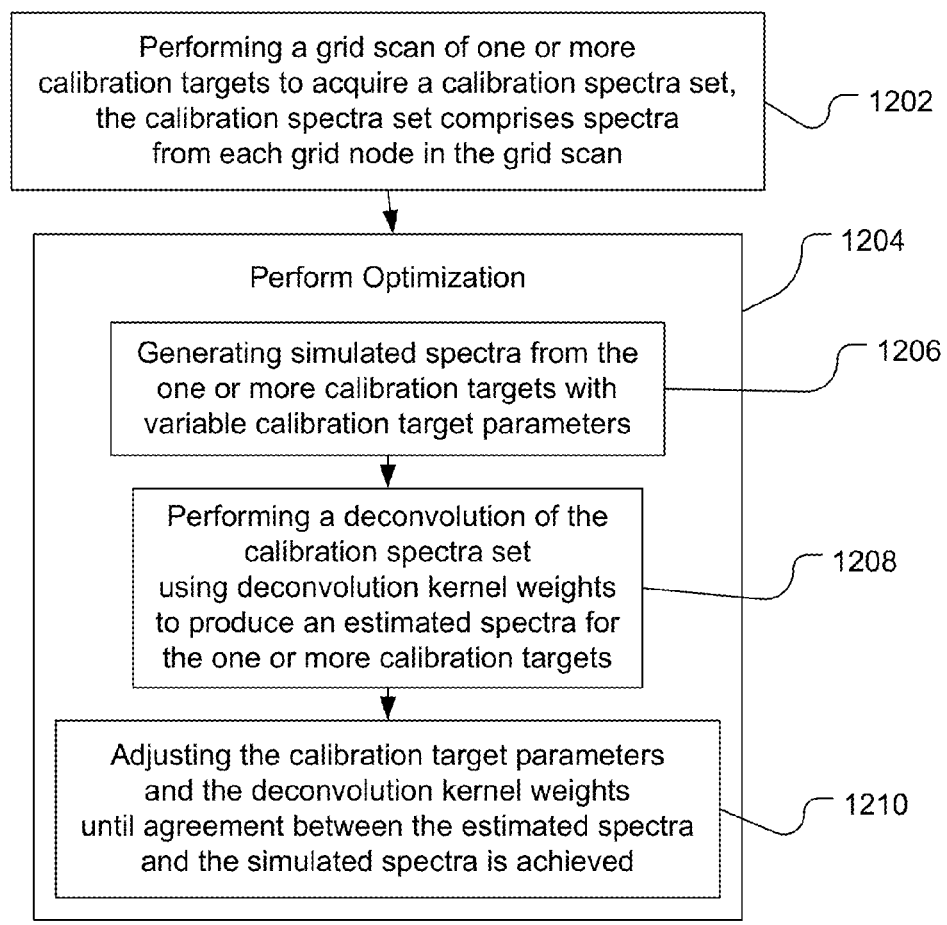
FIG. 12 is a flow chart illustrating a process of determining the deconvolution kernel weights using a calibration procedure that is a combination of experimental and theoretical.

FIG. 12 is a flow chart illustrating a process of determining the weights of the deconvolution kernel using a calibration procedure that is a combination of experimental and theoretical. As illustrated, a grid scan of one or more calibration targets is performed using a spectroscopic metrology device to acquire a calibration spectra set (1202), as discussed above in FIG. 7. The "true" target spectrum from the one or more calibration targets in the present calibration procedure, however, is unknown. Accordingly, an optimization process is performed (1204), e.g., the Levenberg-Marquardt or other similar algorithm. The optimization process includes generating simulated spectra from the one or more calibration targets with variable calibration target parameters (1206). A deconvolution of the calibration spectra set is performed using deconvolution kernel weights to produce an estimated spectra for the one or more calibration targets (1208). The calibration target parameters and the deconvolution kernel weights are adjusted until agreement between the estimated spectra and the simulated spectra is achieved (1210).

By way of example, a combination experimental and theoretical calibration procedure may be used to determine the deconvolution kernel weights for an example in which a 5×5 grid scan of multiple calibration targets is performed, as discussed in reference to FIG. 8 above, but where the "true" spectra $Y_o^{(t)}$ of the calibration targets is not known and cannot be measured, e.g., using the twin targets associated with the calibration targets. By way of example, the calibration targets may be made of a thin film of $SiO_2$ on a monocrystalline Si substrate. While the exact thickness of the thin film for each calibration target may be unknown, the spectrum produced by the calibration target may be accurately simulated for a given oxide thickness. The thickness of the $SiO_2$ film of calibration target "t" is denoted $h_t$ and the simulated spectrum is denoted by $Y_s(h_t)$. Accordingly, equation 3 may be re-written as:

$$Y_o(h_t) = \sum_{d=1}^{25} w_d \cdot Y_d^{(t)}. \qquad \text{eq. 6}$$

If the spectra from the calibration targets is measured with, e.g., 100 wavelengths data-points, equation 6, in fact, represents a system of 100×30 equations, where the unknowns are 100×25 weights and 30 thicknesses. This system of equations can be solved numerically to obtain the weights, as well as the thicknesses.

With the deconvolution kernel weights determined, as discussed above, or using any other desired procedure, the small spot by deconvolution process may be used to reduce the effective spot size of the measurement spot from the optical metrology device. The implementation of the deconvolution process, however, requires acquisition of a large number of spectra in a grid scan, e.g., N×N spectra for each measurement. Performing a full grid scan of the measurement target to acquire the N×N spectra for each measurement, however, will introduce a significant degradation of the measurement throughput.

To increase measurement throughput, sparse sampling of the grid scan may be employed where spectra from less than all of the grid nodes in the grid scan is collected from the measurement target. For example, the spectra may not be measured from the measurement target at grid nodes having relatively weak weights with respect to the weight of the grid node centered on the measurement target or from grid nodes aligned with neighborhood locations that are not significantly more reflective than the measurement target. In one implementation, only the spectrum from the grid node centered over the measurement target may be collected. In other embodiments, spectra from the measurement target may be collected from a plurality of grid nodes, but less than all of the grid nodes. The remaining spectra, i.e., the spectra from grid nodes that are not collected from the measurement target, may be provided from a training target. The training target should be similar to the measurement target, e.g., produced using the same fabrication process, so that the training target and measurement target, as well as the neighborhood locations around the targets themselves, have the same materials and geometries. A training target may be on a different wafer, e.g., from a training wafer, that is produced with the same fabrication process as the measurement target. Alternatively, the training target may be a selected target that is on the same wafer as the measurement target, e.g., where a training target on the wafer is used to acquire the training spectra set, and one or more measurement targets on the same wafer are measured using sparse sampling.

Sparse sampling for the deconvolution process may be used if the training target and measurement target are similar, i.e., the measurement target and its neighborhood locations are similar to the training targets and their neighborhood locations. Additionally, sparse sampling of the grid scan of the measurement target may be used if the weights $w_q$ of the grid nodes "q," which are the grid nodes that will not be sampled for the measurement target, are small when compared with the weight associated to the grid node at the center of the target and the signals acquired from the training target from the grid nodes q are not significantly larger than the signal acquired at the grid node at the center of the target. By way of example, one way to determine whether the weights and signals are sufficiently small that a grid node may be included in the set of grid nodes q during sparse sampling of the measurement target is provided by:

$$\sum_p w_p \cdot Z_p^{(t)} \gtrapprox 10 \cdot \sum_q w_q \cdot Z_q^{(t)}. \qquad \text{eq. 7}$$

where "p" are the grid nodes to be sampled on the measurement target, and include at least the grid node at the center of the target and "q" are the grid nodes that will not be sampled on the measurement target, and $Z_p$ and $Z_q$ are the spectra from the training target at grid node(s) p and grid node q. Under these conditions, sparse sampling may provide a good approximation of the "true" spectrum of the measurement target, which will increase considerably the measurement throughput.

Figure 13:
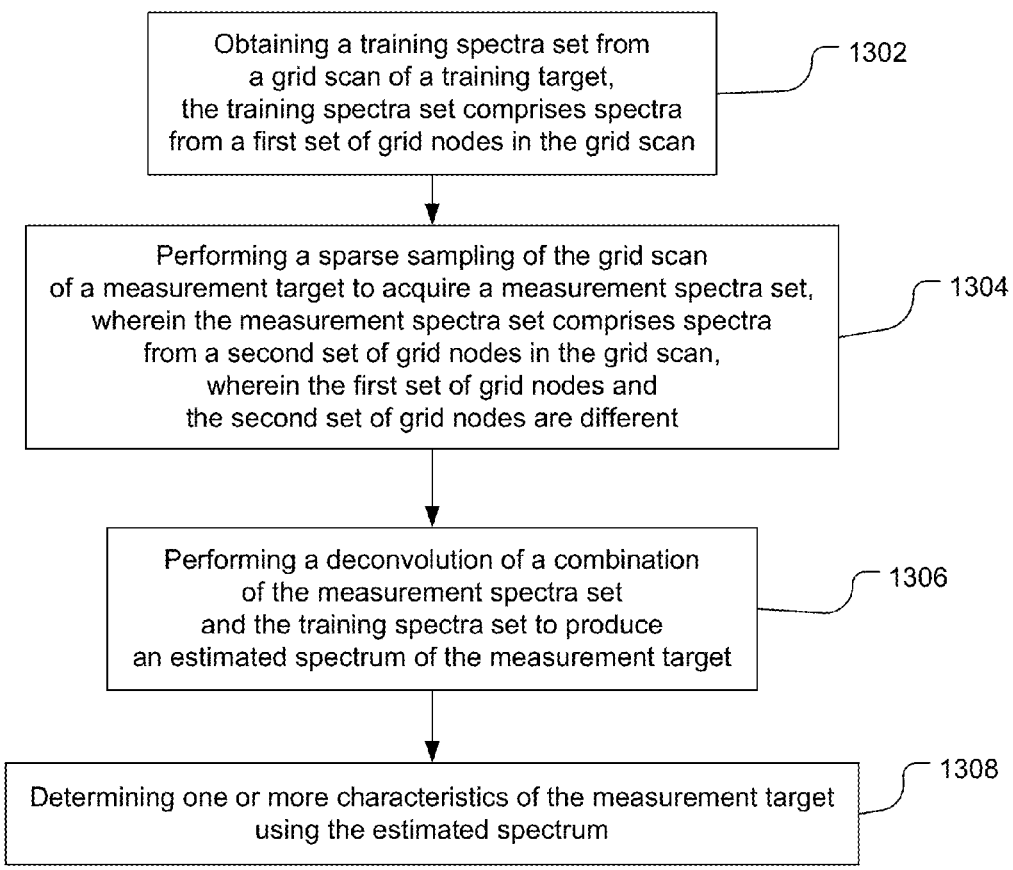
FIG. 13 is a flow chart illustrating the process of small spot by deconvolution using sparse sampling of the grid scan of the measurement target.

FIG. 13 is a flow chart illustrating the process of small spot by deconvolution using sparse sampling of the grid scan of the measurement target. As illustrated in FIG. 13, a training spectra set from a grid scan of a training target is obtained (1302). The grid scan of the training target is performed using a spectroscopic metrology device with incident light having a measurement spot size. For example, the measurement spot size may be larger than desired, i.e., larger than the training target. The training spectra set includes spectra from a first set of grid nodes in the grid scan. For example, the first set of grid nodes may include all grid nodes except the grid node aligned with the center of the training target. Alternatively, the first set of grid nodes may include all grid nodes except the grid node aligned with the center of the training target and one or more grid nodes aligned with locations having small weights compared with the weight associated to the grid node at the center of the target or locations that produce signals that are significantly larger than the signal acquired at the grid node at the center of the measurement target.

A sparse sampling of the grid scan of a measurement target is performed to acquire a measurement spectra set (1304). The sparse sampling is performed using the same spectroscopic metrology device that is used to perform the grid scan of the training target. The measurement spectra set includes spectra from a second set of grid nodes in the grid scan, wherein the first set of grid nodes and the second set of grid nodes are different. The grid scan of the measurement target is the same as the grid scan of the training target, i.e., the positions of the grid nodes relative to the training target in the grid scan of the training target are the same as the positions of the grid nodes relative to the measurement target in the grid scan of the measurement target. The sparse sampling of the grid scan of the measurement target acquires the spectrum from a grid node that is aligned with a center of the measurement target. Thus, by way of example, the second set of grid nodes may include only the grid node aligned with the center of the measurement target and, thus, the measurement spectra set may include only a single spectrum. If desired, the sparse sampling of the grid scan of the measurement target may acquire additional spectra, such as a second spectrum from a second grid node that is aligned with a location with respect to the measurement target that has a small weight compared to the weight associated to the grid node at the center of the target or locations or that produces signals that are significantly larger than the signal acquired at the grid node at the center of the measurement target. Thus, the measurement spectra set may include a plurality of spectra.

A deconvolution of a combination of the measurement spectra set and the training spectra set is performed to produce an estimated spectrum of the measurement target that is an estimate of the spectrum from the measurement target produced using incident light having an effective measurement spot size that is smaller than the measurement spot size (1306). As discussed above, a linear or non-linear deconvolution may be used. The deconvolution of the combined measurement spectra set and the training spectra set uses a deconvolution kernel weight for each grid node in the grid scan that may be previously obtained. As discussed above, the deconvolution kernel weight for each grid node in the grid scan may be obtained theoretically or experimentally, e.g., using a calibration spectra set acquired from a grid scan of one or more calibration targets, or a combination of theoretically or experimentally. The grid scan of the measurement target is the same as the grid scan of the calibration target (if used), i.e., the positions of the grid nodes relative to the calibration target are the same as the positions of the grid nodes relative to the measurement target. The result of the deconvolution of the combined measurement spectra set and the training spectra set is an estimated spectrum of the measurement target that is an estimate of a spectrum from the measurement target produced using incident light with an effective measurement spot size that is smaller than the measurement spot size. For example, if the measurement spot size is larger than the measurement target, the deconvolution of the measurement spectra set and the training spectra set may produce an effective measurement spot size that is smaller than the measurement target. One or more characteristics of the measurement target may then be determined using the estimated spectrum of the measurement target (1308). One or more of the results of the above-process steps, e.g., including the training spectra set, the measurement spectra set, the estimated spectrum, and the one or more characteristics of the measurement target is stored in memory, e.g., may be stored at least temporarily in memory 154 or in non-transitory computer-usable storage medium 160 for processing and/or to provide results to an end user.

In one example of small spot by deconvolution using sparse sampling of the grid scan of the measurement target, deconvolution kernel weights $w_d$ may be obtained as discussed above. The weight associated with the grid node aligned with the center of the measurement target (and training target) may be denoted as weight $w_1$. In this example, weight $w_1$ is significantly higher than all other weights $w_d$, e.g., the difference between weight $w_1$ and any other weight $w_d$ is greater than threshold. Additionally, none of the signals received at the grid nodes during the grid scan of the training target is significantly higher than the signal from the grid node d=1, i.e., at the center of the training target. For example, the difference between signals from non-center grid nodes $Y_{d \neq 1}$ and the signal from the grid node at the center of the training target $Y_1$ is less than a threshold. Thus, sparse sampling may be employed where only the center of the measurement target will be measured.

Figure 14:
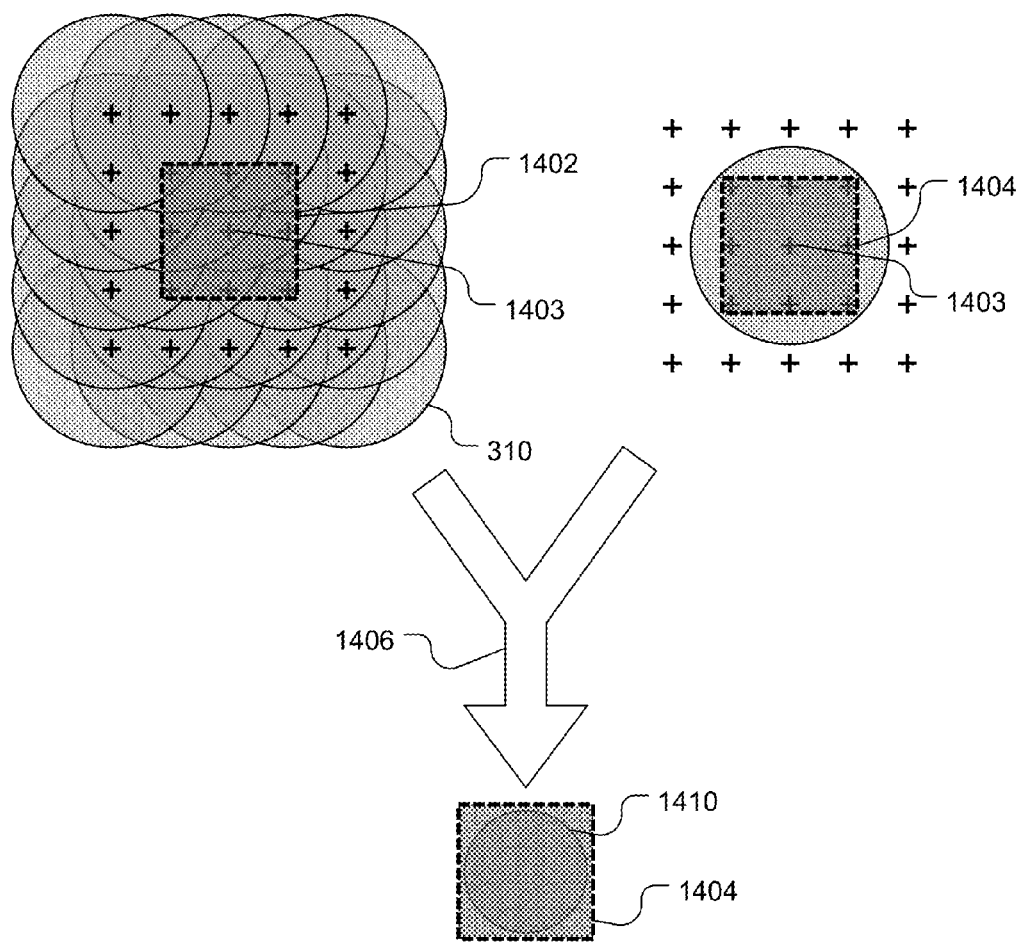
FIG. 14 graphically illustrates the process of small spot by deconvolution using sparse sampling of the grid scan of the measurement target, where a spectrum from one grid node aligned with center of the measurement target is acquired for the measurement spectra set.

FIG. 14 graphically illustrates the process of small spot by deconvolution using sparse sampling of the grid scan of the measurement target, where spectra from only the center grid node, i.e., the grid node 1403 aligned with the center of the measurement target 1404, is acquired and used as the measurement spectra set. A training spectra set is obtained from a training target 1402, which is similar to the measurement target 1404, i.e., the training target 1402 and measurement target 1404, including neighborhood locations, have similar materials and geometries. For example, the training target 1402 may be on the same wafer or on a different wafer from the same fabrication process. If desired, multiple training targets (t) may be used. The training spectra set is obtained from a grid scan of the training target 1402, illustrated in FIG. 14 with a number of measurement spots 310 over a set of grid nodes. In the present example, the training spectra set does not include the spectrum acquired from the grid node 1403 aligned with the center of the training target 1402. The training spectra set, denoted as $Z_d^{(t)}$, is saved for subsequent use.

A sparse sampling is performed of the grid scan of a measurement target 1404 to acquire a measurement spectra set. In this example, and as illustrated in FIG. 14, the sparse sampling is performed by measuring the spectrum from the measurement target 1404 at only grid node 1403 aligned with the center of the measurement target 1404. The measurement spectra set may be denoted as $Y_d$ where the index "d" has only one value, say d=1. As illustrated with arrow 1406 deconvolution of the combined training spectra set $Z_d$ and the measurement spectra set $Y_d$ may produce an estimated spectrum of the measurement target that is an estimate of a spectrum from the measurement target produced with incident light having an effective measurement spot size 1410 that is smaller than the measurement target 1404. The estimated spectrum of the measurement target may be given by the following equation, for each wavelength:

$$Y_o = w_1 \cdot Y_1 + \sum_{d=2}^{25} w_d \cdot Z_d. \qquad \text{eq. 8}$$

In another example, deconvolution kernel weights $w_d$ may be obtained as discussed above. The grid nodes of the grid scan may be split into two sets denoted as "p" and "q," where set p includes the grid node that is aligned with the center of the target. In this example, any grid node having a weight that is not significantly less than the weight of the grid node aligned with the center of the target, i.e., the difference is less than a threshold, is included in set p. Additionally, any grid node with a received signal that is significantly higher than the received signal at the grid node at the center of the training target is also included in set p. Accordingly, grid nodes in set q will include grid nodes with weights that are much less than the weights of the grid nodes in set p, i.e., $w_q \ll w_p$ and their respective signals, $Y_p$ are not much greater than the received signals from the grid nodes in set p, i.e., $(Y_q \gg Y_p)!$, where "!" represents the logical negation. Thus, sparse sampling may be employed where the grid scan of the measurement target is reduced to only the "p" grid nodes.

Figure 15:
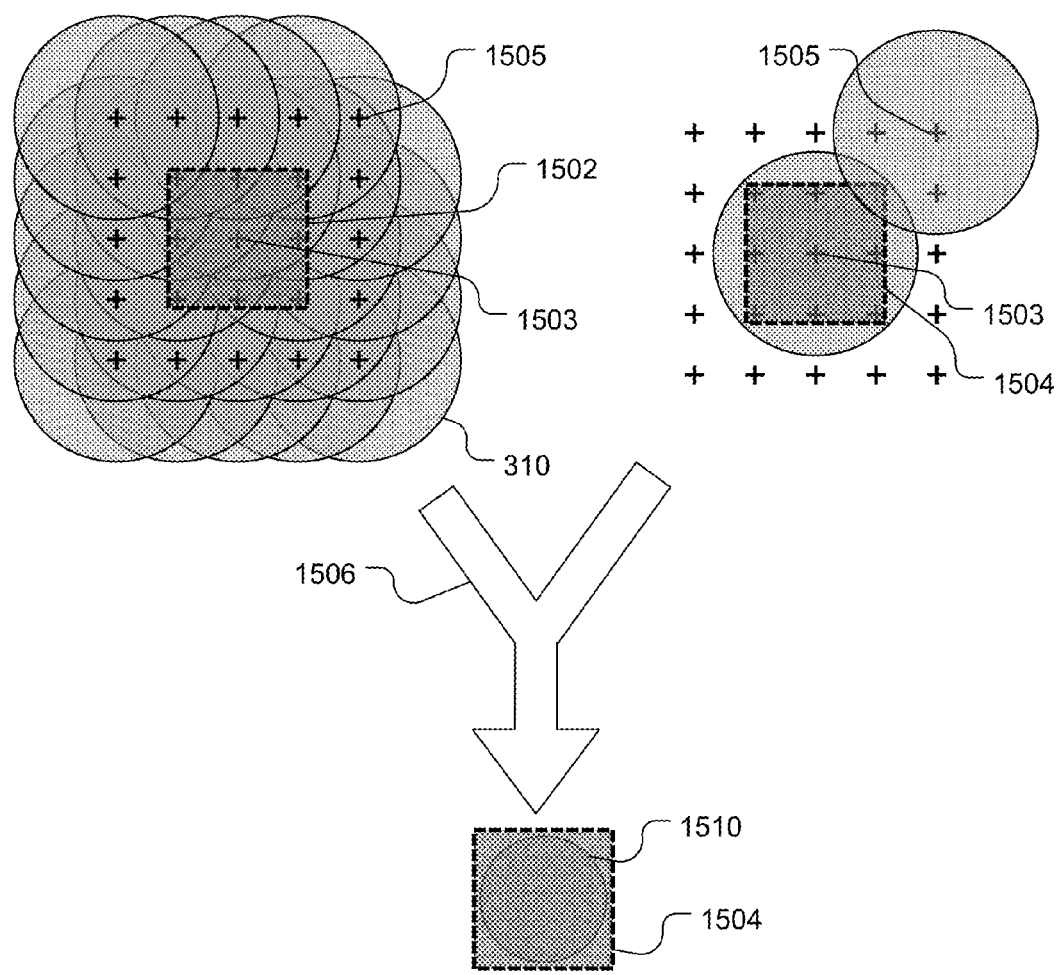
FIG. 15 graphically illustrates the process of small spot by deconvolution using sparse sampling of the grid scan of the measurement target, where spectra from a plurality of grid nodes is acquired and used as the measurement spectra set.

FIG. 15 graphically illustrates the process of small spot by deconvolution using sparse sampling of the grid scan of the measurement target, where spectra from only "p" grid nodes of the grid scan of the measurement target are measured and used as the measurement spectra set. Similar to FIG. 14, a training spectra set is obtained from a training target 1502, this is similar to the measurement target 1504. The training spectra set is obtained from a grid scan of the training target 1502, illustrated in FIG. 15 with a number of measurement spots 310 over a set of grid nodes. In the present example, the grid node 1505 may have a weight that is not much less than the weight for the grid node 1503, which is aligned with the center of the target. Alternatively, the signal from grid node 1505 may be much greater than the signal received at the grid node 1503, i.e., the neighborhood location associated with grid node 1505 may be more reflective than the training target 1502. Thus, in the present example, the training spectra set includes spectra from the set q of grid nodes, and accordingly does not include the spectra acquired from grid nodes 1503 or 1505. The training spectra set, denoted as $Z_q$ is saved for subsequent use.

A sparse sampling is performed of the grid scan of a measurement target 1504 to acquire the measurement spectra set. In this example, and as illustrated in FIG. 15, the sparse sampling is performed by measuring the spectrum from the measurement target 1504 at the set p of grid nodes, i.e., at the grid node 1503 aligned with the center of the measurement target 1504 and grid node 1505. The measurement spectra set may be denoted as $Y_p$. As illustrated with arrow 1506 deconvolution of the combined training spectra set $Z_d$ and the measurement spectra set $Y_p$ may produce an estimated spectrum that is an estimate of a spectrum from the measurement target produced with incident light having an effective measurement spot size 1510 that is smaller than the measurement target 1504. The estimated spectrum of the measurement target may be given by the following equation, for each wavelength:

$$Y_o = \sum_p w_p \cdot Y_p + \sum_q w_q \cdot Z_q. \qquad \text{eq. 9}$$

Once the estimated spectrum for the measurement target is produced using small spot by deconvolution to reduce the effective spot size of the measurement spot, one or more characteristics of the measurement target may then be conventionally determined using the estimated spectrum of the measurement target.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of spectroscopic metrology, the method comprising:
    obtaining a training spectra set from a grid scan of a training target, wherein the grid scan of the training target is performed using a spectroscopic metrology device with incident light having a measurement spot size, wherein the training spectra set comprises spectra from a first set of grid nodes in the grid scan;
    performing a sparse sampling of the grid scan of a measurement target using the spectroscopic metrology device with the incident light having the measurement spot size to acquire a measurement spectra set, wherein the measurement spectra set comprises spectra from a second set of grid nodes in the grid scan;
    performing a deconvolution of a combination of the measurement spectra set and the training spectra set to produce an estimated spectrum of the measurement target that is an estimate of a spectrum from the measurement target produced with the incident light having an effective measurement spot size that is smaller than the measurement spot size; and
    determining one or more characteristics of the measurement target using the estimated spectrum.

2. The method of claim 1, wherein grid nodes of the grid scan of the measurement target have a same position and a same orientation with respect to the measurement target as the grid nodes of the grid scan of the training target with respect to the training target.

3. The method of claim 1, wherein the first set of grid nodes is complementary to the second set of grid nodes.

4. The method of claim 1, wherein performing the deconvolution of the combination of the measurement spectra set and the training spectra set comprises performing one of a linear or a non-linear deconvolution.

5. The method of claim 1, wherein the sparse sampling of the grid scan of the measurement target comprises acquiring a spectrum from a first grid node aligned with a center of the measurement target, wherein the measurement spectra set comprises only the spectrum from the first grid node.

6. The method of claim 1, wherein the sparse sampling of the grid scan of the measurement target comprises acquiring a first spectrum from a first grid node aligned with a center of the measurement target and a second spectrum from a second grid node that is not aligned with the center of the measurement target, wherein the measurement spectra set comprises at least the first spectrum and the second spectrum.

7. The method of claim 6, wherein the second grid node is aligned with a location that is more reflective than the center of the measurement target.

8. The method of claim 1, wherein the sparse sampling of the grid scan of the measurement target further comprises acquiring a plurality of spectra from a plurality of grid nodes with respect to the measurement target, wherein the plurality of grid nodes is less than all of the grid nodes of the grid scan, wherein the measurement spectra set comprises the plurality of spectra.

9. The method of claim 1, wherein the training target has a same material and geometry configuration as the measurement target and neighborhood locations around the training target has a same material and geometry configuration as neighborhood locations around the measurement target.

10. The method of claim 9, wherein the training target is on a different sample than the measurement target.

11. The method of claim 9, wherein the training target is on a same sample as the measurement target.

12. The method of claim 1, wherein obtaining the training spectra set from the grid scan of the training target comprises:
performing the grid scan of the training target using the spectroscopic metrology device to acquire spectra from each grid node in the grid scan;
identifying the second set of grid nodes in the grid scan using the spectra from each grid node; and
storing the spectra from grid nodes that are not n the second set of grid nodes in the training spectra set.

13. The method of claim 12, wherein the spectra from each grid node in the grid scan includes a spectrum from a first grid node aligned with a center of the training target, wherein identifying the second set of grid nodes in the grid scan using the spectra from each grid node comprises comparing a weighted spectrum from the first grid node to combined weighted spectra from remaining grid nodes.

14. The method of claim 1, further comprising obtaining a deconvolution kernel weight for each grid node in the grid scan, wherein the deconvolution of the combination of the measurement spectra set and the training spectra set uses the deconvolution kernel weight for each grid node.

15. The method of claim 14, wherein obtaining the deconvolution kernel weight for each grid node in the grid scan comprises:
obtaining a point spread function for an optical system of the spectroscopic metrology device; and
inverting the point spread function to determine the deconvolution kernel weight for each grid node in the grid scan.

16. The method of claim 14, wherein obtaining the deconvolution kernel weight for each grid node in the grid scan comprises:
performing the grid scan on one or more calibration targets using the spectroscopic metrology device to acquire a calibration spectra set, wherein the calibration spectra set comprises spectra from each grid node in the grid scan;
obtaining spectra from one or more twin targets associated with the one or more calibration targets, wherein each twin target has a same material and geometry configuration as a calibration target with which the twin target is associated and each twin target is larger than the measurement spot size; and
using the calibration spectra set, the spectra measured from the one or more twin targets and an inverted deconvolution formula to calculate the deconvolution kernel weight for each grid node in the grid scan.

17. The method of claim 14, wherein obtaining the deconvolution kernel weight for each grid node in the grid scan comprises:
performing the grid scan on one or more calibration targets using the spectroscopic metrology device to acquire a calibration spectra set, wherein the calibration spectra set comprises spectra from each grid node in the grid scan;
obtaining spectra from one or more twin targets associated with the one or more calibration targets, wherein each twin target has a same material and geometry configuration as a calibration target with which the twin target is associated and each twin target is larger than the measurement spot size;
obtaining spectra from one or more neighborhood locations around the one or ore calibration targets;
using the calibration spectra set, the spectra measured from the one or more twin targets, the spectra measured from the one or more neighborhood locations to calculate a point spread function for an optical system of the spectroscopic metrology device; and
inverting the point spread function to determine the deconvolution kernel weight for each grid node in the grid scan.

18. The method of claim 14, wherein obtaining the deconvolution kernel weight for each and node in the grid scan comprises:
performing the grid scan on one or more calibration targets using the spectroscopic metrology device to acquire a calibration spectra set, wherein the calibration spectra set comprises spectra from each grid node in the grid scan;
performing an optimization process comprising:
generating simulated spectra from the one or more calibration targets with variable calibration target parameters;
performing a deconvolution of the calibration spectra set using deconvolution kernel weights to produce an estimated spectra for the one or more calibration targets;
adjusting the variable calibration target parameters and the deconvolution kernel weights until agreement between the estimated spectra and the simulated spectra is achieved.

19. The method of claim 1, wherein the spectroscopic metrology device is one of a spectroscopic reflectometer and a spectroscopic ellipsometer.

20. A spectroscopic metrology device comprising:
a broadband illumination source to produce broadband illumination;
an optical system that focuses the broadband illumination into incident light with a measurement spot size;
a spectrometer that detects a spectrum of the broadband illumination after being incident on a sample; and
a processor coupled to receive the spectrum from the spectrometer, the processor configured to cause the optical system and the spectrometer to perform a grid scan of a training target to obtain a training spectra set, wherein the training spectra set comprises spectra from a first set of grid nodes in the grid scan; the processor further configured to cause the optical system and the spectrometer to perform a sparse sampling of the grid scan of a measurement target to acquire a measurement spectra set, wherein the measurement spectra set comprises spectra from a second set of grid nodes in the grid scan; to perform a deconvolution of a combination of the measurement spectra set and the training spectra set to produce an estimated spectrum of the measurement target that is an estimate of a spectrum from the measurement target produced with the incident light having an effective measurement spot size that is smaller than the measurement spot size; and to determine one or more characteristics of the measurement target using the estimated spectrum.

21. The spectroscopic metrology device of claim 20, wherein grid nodes of the grid scan of the measurement target have a same position and a same orientation with respect to the measurement target as the grid nodes of the grid scan of the training target with respect to the training target.

22. The spectroscopic metrology device of claim 20, wherein the first set of grid nodes is complementary to the second set of grid nodes.

23. The spectroscopic metrology device of claim 20, wherein the deconvolution is one of a linear or a non-linear deconvolution.

24. The spectroscopic metrology device of claim 20, wherein the processor is configured to cause the optical system and the spectrometer to perform the sparse sampling of the grid scan of the measurement target by being configured to cause the optical system and the spectrometer to acquire a spectrum from a first grid node aligned with a center of the measurement target, wherein the measurement spectra set comprises only the spectrum from the first grid node.

25. The spectroscopic metrology device of claim 20, wherein the processor is configured to cause the optical system and the spectrometer to perform the sparse sampling of the grid scan of the measurement target by being configured to cause the optical system and the spectrometer to acquire a first spectrum from a first grid node aligned with a center of the measurement target and a second spectrum from a second grid node that is not aligned with the center of the measurement target, wherein the measurement spectra set comprises at least the first spectrum and the second spectrum.

26. The spectroscopic metrology device of claim 25, wherein the second grid node is aligned with a location that is more reflective than the center of the measurement target.

27. The spectroscopic metrology device of claim 20, wherein the processor is configured to cause the optical system and the spectrometer to perform the sparse sampling of the grid scan of the measurement target by being configured to cause the optical system and the spectrometer to acquire a plurality of spectra from a plurality of grid nodes with respect to the measurement target, wherein the plurality of grid nodes is less than all of the grid nodes of the grid scan, wherein the measurement spectra set comprises the plurality of spectra.

28. The spectroscopic metrology device of claim 20, wherein the training target has a same material and geometry configuration as the measurement target and neighborhood locations around the training target has a same material and geometry configuration as neighborhood locations around the measurement target.

29. The spectroscopic metrology device of claim 28, wherein the training target is on a different sample than the measurement target.

30. The spectroscopic metrology device of claim 28, wherein the training target is on a same sample as the measurement target.

31. The spectroscopic metrology device of claim 20, wherein the processor is configured to cause the optical system and the spectrometer to perform the grid scan of the training target to obtain the training spectra set by being configured to perform the grid scan of the training target to acquire spectra from each grid node in the grid scan; to identify the second set of grid nodes in the grid scan rising the spectra from each grid node and to store the spectra from grid nodes that are not in the second set of grid nodes in the training spectra set.

32. The spectroscopic metrology device of claim 31, wherein the spectra from each grid node in the grid scan includes a spectrum from a first grid node aligned with a center of the training target, wherein the processor is configured to identify the second set of grid nodes in the grid scan using the spectra from each grid node by being configured to compare a weighted spectrum from the first grid node to combined weighted spectra from remaining grid nodes.

33. The spectroscopic metrology device of claim 20, wherein the processor is further configured to obtain a deconvolution kernel weight for each grid node in the grid scan, wherein the deconvolution of the combination of the measurement spectra set and the training spectra set uses the deconvolution kernel weight for each grid node.

34. The spectroscopic metrology device of claim 33, wherein the deconvolution kernel weight for each grid node in the grid scan is obtained from an inverted point spread function of the optical system.

35. The spectroscopic metrology device of claim 33, wherein the processor is further configured to obtain the deconvolution kernel weight for each grid node in the grid scan by being configured to cause the optical system and the spectrometer to perform the grid scan on one or more calibration targets to acquire a calibration spectra set, wherein the calibration spectra set comprises spectra from each grid node in the grid scan; to cause the optical system and the spectrometer to obtain spectra from one or more twin targets associated with the one or more calibration targets, wherein each twin target has a same material and geometry configuration as a calibration target with which the twin target is associated and each twin target is larger than the measurement spot size; and to use the calibration spectra set, the spectra measured from the one or more twin targets and an inverted deconvolution formula to calculate the deconvolution kernel weight for each grid node in the grid scan.

36. The spectroscopic metrology device of claim 33, wherein the processor is further configured to obtain the deconvolution kernel weight for each grid node in the grid scan by being configured to cause the optical system and the spectrometer to perform the grid scan on one or more calibration targets to acquire a calibration spectra set, wherein the calibration spectra set comprises spectra from each grid node in the grid scan; to cause the optical system and the spectrometer to obtain spectra from one or more twin targets associated with the one or more calibration targets, wherein each twin target has a same material and geometry configuration as a calibration target with which the twin target is associated and each twin target is larger than the measurement spot size; to cause the optical system and the spectrometer to obtain spectra from one or more neighborhood locations around the one or more calibration targets; to use the calibration spectra set, the spectra measured from the one or more twin targets, the spectra measured from the one or more neighborhood locations to calculate a point spread function for the optical system; and wherein the deconvolution kernel weight for each grid node in the grid scan is obtained from an inversion of the point spread function of the optical system.

37. The spectroscopic metrology device of claim 33, wherein the processor is further configured to obtain the deconvolution kernel weight for each grid node in the grid scan by being configured to perform the grid scan on one or more calibration targets to acquire a calibration spectra set, wherein the calibration spectra set comprises spectra from each grid node in the grid scan; and to perform an optimization process by being configured to generate simulated spectra from the one or more calibration targets with variable calibration target parameters; perform a deconvolution of the calibration spectra set using deconvolution kernel weights to produce an estimated spectra for the one or more calibration targets; and to adjust the variable calibration target parameters and the deconvolution kernel weights until agreement between the estimated spectra and the simulated spectra is achieved.

38. The spectroscopic metrology device of claim 20, wherein the spectroscopic metrology device is one of a spectroscopic reflectometer and a spectroscopic ellipsometer.

39. A method comprising:
producing deconvolution kernel weights for deconvolution of spectral signals from a spectroscopic metrology device, wherein producing the deconvolution kernel weights comprises:
performing a grid scan of one or more calibration targets using the spectroscopic metrology device using incident light having a measurement spot size to acquire a calibration spectra set, wherein the grid scan comprises a plurality of grid nodes and wherein the calibration spectra set comprises spectra from each grid node in the grid scan; and
using the calibration spectra set to determine a deconvolution kernel weight for each grid node in the grid scan;
produce an estimated spectrum of a measurement target comprising:
obtaining a training spectra set from the grid scan of a training target, wherein the grid scan of the training target is performed using the spectroscopic metrology device with the incident light having the measurement spot size, wherein the training spectra set comprises spectra from a first subset of the plurality of grid nodes;
performing a sparse sampling of the grid scan of the measurement target using the spectroscopic metrology device with the incident light having the measurement spot size to acquire a measurement spectra set, wherein the measurement spectra set comprises spectra a second subset of the plurality of grid nodes;
performing a deconvolution of a combination of the measurement spectra set and the training spectra set using the deconvolution kernel weight for each grid node in the grid scan to produce the estimated spectrum of the measurement target that is an estimate of a spectrum from the measurement target produced with the incident light having an effective measurement spot size that is smaller than the measurement spot size; and
determining one or more characteristics of the measurement target using the estimated spectrum.

40. The method of claim 39, further comprising:
obtaining spectra from one or more twin targets associated with the one or more calibration targets, wherein each twin target has a same material and geometry configuration as a calibration target with which the twin target is associated and each twin target is larger than a measurement spot size of the spectroscopic metrology device; and
wherein using the calibration spectra set to determine the deconvolution kernel weight for each grid node in the grid scan comprises using the calibration spectra set, the spectra measured from the one or more twin targets and an inverted deconvolution formula to calculate the deconvolution kernel weight for each grid node in the grid scan.

41. The method of claim 39, further comprising:
obtaining spectra from one or more twin targets associated with the one or more calibration targets, wherein each twin target has a same material and geometry configuration as a calibration target with which the twin target is associated and each twin target is larger than a measurement spot size of the spectroscopic metrology device;
obtaining spectra from one or more neighborhood locations around the one or more calibration targets;
wherein using the calibration spectra set to determine the deconvolution kernel weight for each grid node in the grid scan comprises:
using the calibration spectra set, the spectra measured from the one or more twin targets, the spectra measured from the one or more neighborhood locations to calculate a point spread function for an optical system of the spectroscopic metrology device; and
inverting the point spread function to determine the deconvolution kernel weight for each grid node in the grid scan.

42. The method of claim 39, wherein using the calibration spectra set to determine the deconvolution kernel weight for each grid node in the grid scan comprises performing an optimization process comprising:
generating simulated spectra from the one or more calibration targets with variable calibration target parameters;
performing a deconvolution of the calibration spectra set using deconvolution kernel weights to produce an estimated spectra for the one or more calibration targets;
adjusting the variable calibration target parameters and the deconvolution kernel weights until agreement between the estimated spectra and the simulated spectra is achieved.

* * * * *

UNITED STATES PATENT AND TRADEMARK OFFICE
CERTIFICATE OF CORRECTION

PATENT NO. : 9,958,327 B2
APPLICATION NO. : 14/505373
DATED : May 1, 2018
INVENTOR(S) : Amit Shachaf, Pedro Vagos and Michael Elad It is certified that error appears in the above-identified patent and that said Letters Patent is hereby corrected as shown below:

In the Claims

In Column 17, Line 16, in Claim 12, after "nodes that are not" delete "n" and insert --in--.

In Column 18, Line 4, in Claim 17, after "around the one or" delete "ore" and insert --more--.

In Column 18, Line 14, in Claim 18, after "weight for each" delete "and" and insert --grid--.

In Column 19, Line 61, in Claim 31, after "the grid scan rising" delete "rising" and insert --using--.

Signed and Sealed this
Twenty-eighth Day of May, 2019

Andrei Iancu
*Director of the United States Patent and Trademark Office*